US012558214B2

(12) United States Patent
Qureshi et al.

(10) Patent No.: US 12,558,214 B2
(45) **Date of Patent: \*Feb. 24, 2026**

(54) INTRAOCULAR LENS SYSTEM

(71) Applicant: SHARPVIEW OPHTHALMOLOGY LIMITED, London (GB)

(72) Inventors: M Qureshi, London (GB); Pablo Artal, London (GB); Robbie Scott, London (GB); Juan Tabernero, London (GB)

(73) Assignee: SHARPVIEW OPHTHALMOLOGY LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,032

(22) Filed: Mar. 24, 2023

(65) Prior Publication Data

US 2023/0293290 A1 Sep. 21, 2023

Related U.S. Application Data

(63) Continuation of application No. 17/188,793, filed on Mar. 1, 2021, now Pat. No. 11,633,274, which is a
(Continued)

(30) Foreign Application Priority Data

Aug. 12, 2013 (GB) ...................................... 1314428
Mar. 20, 2014 (GB) ...................................... 1405005
Jul. 24, 2014 (GB) ...................................... 1413158

(51) Int. Cl.
*A61F 2/16* (2006.01)

(52) U.S. Cl.
CPC .......... *A61F 2/1648* (2013.01); *A61F 2/1613* (2013.01); *A61F 2/1637* (2013.01);
(Continued)

(58) Field of Classification Search
CPC ....... A61F 2/164; A61F 2/1648; B29D 11/026
See application file for complete search history.

(56) References Cited

U.S. PATENT DOCUMENTS 3,711,870 A 1/1973 Deitrick
3,866,249 A 2/1975 Flom
(Continued)

FOREIGN PATENT DOCUMENTS

CN 1164652 A 11/1997
CN 1481227 A 3/2004
(Continued)

OTHER PUBLICATIONS

Orzalesi et al, "A Double Intraocular Lens Implant for Visual Rehabilitation of Patients with Macular Disease", The IOL-VIP System, Ophthalmology, vol. 114, No. 5, pp. 860-865, May 2007.
(Continued)

*Primary Examiner* — Javier G Blanco
(74) *Attorney, Agent, or Firm* — John A. Zurawski; The Belles Group, P.C.

(57) ABSTRACT

A lens for use in an intraocular lens system for treating age-related macular degeneration (AMD), the lens including an anterior surface, a posterior surface, and a plurality of haptics configured to align the anterior light-converging intraocular lens with an optical axis of the eye. The plurality of haptics may have a symmetrical design and comprising ciliary-sulcus-engaging surfaces configure to position the lens within in a ciliary sulcus of an eye. At least one of the anterior surface and the posterior surface may be rendered as aspherical surfaces selected to induce spherical aberration while minimizing optical aberration and thereby provide for a continuum of retinal images to be focused at an area macula of a retina of the eye between two retinal eccentricities.

14 Claims, 9 Drawing Sheets

Related U.S. Application Data continuation of application No. 16/057,210, filed on Aug. 7, 2018, now Pat. No. 10,959,836, which is a continuation of application No. 14/911,937, filed as application No. PCT/GB2014/052459 on Aug. 12, 2014, now abandoned.

(52) U.S. Cl.
CPC ............ *A61F 2/164* (2015.04); *A61F 2/1651* (2015.04); *A61F 2/1656* (2013.01); *A61F 2002/1683* (2013.01); *A61F 2002/1689* (2013.01); *A61F 2002/169* (2015.04); *A61F 2002/1696* (2015.04); *A61F 2002/1699* (2015.04)

(56) References Cited

U.S. PATENT DOCUMENTS

| | | | |
|---|---|---|---|
| 3,913,148 A | 10/1975 | Potthast | |
| 3,925,825 A | 12/1975 | Richards et al. | |
| 4,014,049 A | 3/1977 | Richards et al. | |
| 4,041,552 A | 8/1977 | Ganias | |
| 4,053,953 A | 10/1977 | Flom et al. | |
| 4,253,199 A | 3/1981 | Banko | |
| 4,254,509 A | 3/1981 | Tennant | |
| 4,285,072 A | 8/1981 | Morcher et al. | |
| 4,409,691 A | 10/1983 | Levy | |
| 4,842,601 A | 6/1989 | Smith | |
| 4,957,506 A | 9/1990 | Mercier | |
| 5,201,762 A | 4/1993 | Hauber | |
| 5,391,202 A | 2/1995 | Lipshitz et al. | |
| 5,674,282 A | 10/1997 | Cumming | |
| 5,796,462 A | 8/1998 | Roffman et al. | |
| 6,596,026 B1 | 7/2003 | Gross et al. | |
| 7,186,266 B2 | 3/2007 | Peyman | |
| 7,662,179 B2 | 2/2010 | Sarfarazi | |
| 7,918,886 B2 | 4/2011 | Aharoni et al. | |
| 8,496,701 B2 | 7/2013 | Hermans et al. | |
| 8,696,746 B2 | 4/2014 | Wanders et al. | |
| 8,770,745 B2 | 7/2014 | Lindacher et al. | |
| 8,858,541 B2 | 10/2014 | Liang | |
| 8,894,203 B2 | 11/2014 | Bradley et al. | |
| 9,675,445 B2 | 6/2017 | Moriarity et al. | |
| 9,757,228 B2 | 9/2017 | Wanders et al. | |
| 9,770,326 B2 | 9/2017 | Bradley et al. | |
| 10,463,473 B2 | 11/2019 | Rombach et al. | |
| 2003/0060881 A1* | 3/2003 | Glick ................... | A61F 2/1629 623/6.37 |
| 2004/0082995 A1 | 4/2004 | Woods | |
| 2004/0156014 A1 | 8/2004 | Piers et al. | |
| 2006/0030938 A1 | 2/2006 | Altmann | |
| 2006/0100704 A1 | 5/2006 | Blake | |
| 2006/0229720 A1 | 10/2006 | Glazier et al. | |
| 2007/0270947 A1 | 11/2007 | Peyman | |
| 2008/0084534 A1 | 4/2008 | Lindacher et al. | |
| 2008/0269890 A1 | 10/2008 | Simpson et al. | |
| 2008/0281414 A1 | 11/2008 | Akahoshi | |
| 2009/0204211 A1 | 8/2009 | Angelopoulos et al. | |
| 2009/0210054 A1 | 8/2009 | Weeber et al. | |
| 2010/0094413 A1 | 4/2010 | Rombach et al. | |
| 2010/0211167 A1 | 8/2010 | Glazier et al. | |
| 2010/0211169 A1 | 8/2010 | Stanley et al. | |
| 2011/0029073 A1* | 2/2011 | Liang ................... | A61F 2/1613 623/5.11 |
| 2011/0032474 A1 | 2/2011 | Lindacher et al. | |
| 2011/0153014 A1 | 6/2011 | Zhang et al. | |
| 2011/0205486 A1 | 8/2011 | Zhao | |
| 2012/0029631 A1 | 2/2012 | Wanders et al. | |
| 2012/0071972 A1 | 3/2012 | Zhao | |
| 2012/0136438 A1 | 5/2012 | Moriarity | |
| 2012/0154740 A1 | 6/2012 | Bradley et al. | |
| 2013/0278888 A1 | 10/2013 | Bakaraju et al. | |
| 2014/0172091 A1 | 6/2014 | Wanders et al. | |
| 2015/0029460 A1 | 1/2015 | Bradley et al. | |
| 2016/0106535 A1 | 4/2016 | Moriarty | |

FOREIGN PATENT DOCUMENTS

| | | |
|---|---|---|
| CN | 1694658 A | 11/2005 |
| CN | 101132747 A | 2/2008 |
| CN | 101523271 A | 9/2009 |
| CN | 101568312 A | 10/2009 |
| CN | 101909539 A | 12/2010 |
| CN | 102395917 A | 3/2012 |
| CN | 102458305 A | 5/2012 |
| GB | 2517531 A | 2/2015 |
| JP | 02198547 A | 8/1990 |
| JP | 2009082723 A | 4/2009 |
| JP | 2010512814 A | 4/2010 |
| JP | 2011511671 A | 4/2011 |
| JP | 2012527929 A | 11/2012 |
| JP | 2013503700 A | 2/2013 |
| JP | 5398089 A | 6/2013 |
| WO | 9107147 A1 | 5/1991 |
| WO | 2004024035 A1 | 3/2004 |
| WO | 2005066694 A2 | 7/2005 |
| WO | 2007047427 A2 | 4/2007 |
| WO | 2007059160 A2 | 5/2007 |
| WO | 2007128423 A1 | 11/2007 |
| WO | 2008137419 A2 | 11/2008 |
| WO | 2009058755 A1 | 5/2009 |
| WO | 2010054255 A1 | 5/2010 |
| WO | 2015022515 A1 | 2/2015 |

OTHER PUBLICATIONS

Third Office Action of the State Intellectual Property Office (SIPO) in the corresponding Chinese Application Np. 2018.2014800537861, issued Sep. 13, 2018.

International Preliminary Report on Patentability for International Application No. PCT/GB2014/052458, mailed Feb. 25, 2016, 12 Pages.

International Preliminary Report on Patentability for International Application No. PCT/GB2014/052459, mailed Feb. 25, 2016, 11 Pages.

International Search Report and Written Opinion for International Application No. PCT/GB2014/052458, mailed Nov. 18, 2014, 16 Pages.

International Search Report and Written Opinion for International Application No. PCT/GB2014/052459, mailed Nov. 14, 2014, 13 Pages.

Office Action for Chinese Application No. 2014800537861, mailed Jan. 19, 2018, 19 Pages.

Office Action for Japanese Application No. 2016533953, mailed Jun. 26, 2018, 8 Pages.

Office Action for Japanese Patent Application No. 2023045595, mailed Jan. 23, 2024, 8 pages.

Search Report for Chinese Application No. 2014800537861, dated Aug. 12, 2014, 2 Pages.

Japanese Office Action, Japanese Patent Application No. 2023-045595, Issued May 14, 2025, 7 pp.

* cited by examiner

Distance between lenses 1.4 mm                    1.7 mm 5 degrees 2.5 degrees 0 degrees

INTRAOCULAR LENS SYSTEM

CROSS-REFERENCE TO RELATED APPLICATIONS

This application is a continuation of U.S. application Ser. No. 17/188,793, filed Mar. 1, 2021, which is a continuation of U.S. application Ser. No. 16/057,210, filed Aug. 7, 2018, now U.S. Pat. No. 10,959,836, issued Mar. 30, 2021, which is a continuation of U.S. application Ser. No. 14/911,937, filed Feb. 12, 2016, which is a 371 National Stage Application of International Application No. PCT/GB2014/052459, filed Aug. 12, 2014, which claims priority to GB Application Number 1314428.2, filed Aug. 12, 2013, GB Application Number 1405005.8, filed Mar. 20, 2014, and GB Application Number 1413158.5, filed Jul. 24, 2014. All of the foregoing are incorporated by reference in their entireties.

FIELD OF THE INVENTION

The present invention relates to an intraocular lens system.

Throughout this application, the terms 'lens' and 'optic' are used interchangeably. It should be understood that optic refers to a refractive component of the intraocular lens.

BACKGROUND

The most common condition affecting the macula is age-related macular degeneration (AMD)-this is also the most common cause of significant visual loss in the developed world. AMD results in loss of the light-sensitive cells (photoreceptors), and supporting tissue at the back of the eye, in a specialised part of the retina known as the macula. The condition most often involves the very central part of the macula (the fovea), an area which enables reading and the recognition of faces. In the majority of patients with age-related macular degeneration loss of vision occurs over a number of years and the pattern of visual loss allows for the maintenance of small islands of functioning photoreceptors in the macula. These remaining islands of tissue may permit sufferers to read but, because the density of light-sensitive cells reduces with increasing eccentricity from the fovea, visual resolution may be impaired such that at 3 degrees nasal to the central fovea, the visual acuity is reduced to 0.4 (compared with a visual acuity of 1.0 at 0 degrees), and at 5 degrees the visual acuity is further reduced to 0.34. Depending on the severity of the disease, patients may benefit from visual aids such as magnifying glasses, or the use of spectacle-mounted or hand-held telescopic devices that facilitate reading. Use of such devices is often restrictive because magnifying glasses are not easily portable (and require good lighting), and telescopic devices can severely reduce a patient's field of view. Despite the problems associated with reduced visual resolution, patients with age-related macular degeneration and similar conditions affecting the central visual field may still make effective use of residual macular tissue outside the damaged fovea (sometimes referred to as the 'preferred retinal locus' or PRL) although this may require the patient to learn to fixate eccentrically—something that is not always easily accomplished. One potential method of improving patients' fixation is to undertake surgery to introduce a device to modify the path of light in the eye such that images are focused on the PRL with or without a magnifying effect. However, the precise location of the PRL varies from patient-to-patient and accurate targeting of the PRL using such an approach is essential if a patient's vision is not to be made worse. Furthermore, as the disease progresses and remaining islands of functioning retina shrink in size, the location of the PRL can shift and it may become necessary to alter the path of light in the eye to take account of this.

Current surgical approaches to the management of poor vision in age-related macular degeneration include the implantation of telescopic lenses, in some cases not dissimilar to those employed for use in cataract surgery. Such lenses have the advantage of superior optics without the disadvantages associated with the use of external telescopic devices. Furthermore, telescopic devices may be configured in such a way as to provide a magnified image that is focused on an area of healthy macula eccentric to the fovea. Most existing designs for these intraocular devices adopt variations on a Galilean telescope system such that a diverging intraocular lens (IOL) is sited in the eye behind a converging IOL.

A basic paraxial approach to an intraocular Galilean telescope is as follows:

$$D = f_{obj} + f_{oc} \left. \atop M = -\frac{f_{oc}}{f_{obj}} \right] \to \left. f_{obj} = D\frac{M}{M-1} \atop f_{oc} = D\frac{M}{M-1} \right]$$

D=distance between lenses (assumed thin lenses)
M=magnification
$f_{obj}$=focal length of the objective lens
$f_{oc}$=focal length of the ocular lens Galilean intraocular telescopes that employ a light-diverging IOL located in the posterior chamber of the eye and a light-converging lens in the anterior chamber of the eye are disclosed by Orzalesi et al. (Ophthalmology Volume 114 Issue 5; 2007) and in U.S. Pat. No. 20120136438 A1. These systems provide for magnification of an image and the deviation of light to target healthier parts of the macula. The latter is achieved by displacement of the diverging lens in a direction perpendicular to the optic axis of the converging lens by means of an asymmetrical haptic design (the haptic is the supporting arm of an IOL, most often seen in pairs with each one attached at opposite sides of the implant to ensure the position of the IOL in the eye remains stable). By shortening one haptic and lengthening the other it is possible to shift the diverging IOL such that a prismatic effect is achieved and light focused eccentric to fixation. The arrangement has a number of disadvantages. Firstly, the prismatic effect is conferred by the diverging IOL, which lies behind the converging IOL in both instances, thereby making access difficult for the purpose of rotating the diverging IOL to target the PRL should its location change at a future date. Secondly, the siting of an IOL in the anterior chamber is known to be associated with secondary pathology such as glaucoma and damage to the cornea of the eye. Thirdly, the optics of such a configuration are highly dependent on the IOLs remaining a fixed distance apart, for the purposes of magnification, and at a fixed displacement perpendicular to the optical axis (in the case of the diverging lens) for the purposes of targeting the PRL so that without consideration of the optimal configuration of the IOLs in relation to one another the system has the potential to make a patient's vision even worse.

Intraocular telescopes that take advantage of IOLs placed in fixed alignment are disclosed in U.S. Pat. Nos. 7,186,266; 6,596,026; 5,391,202; 7,918,886; 20040082995 and 20110153014. The principal disadvantages of fixing the diverging lens to the converging lens in these systems are that: 1) The arrangement may not permit the displacement of one lens in relation to the other to create the prismatic effect necessary to target the PRL (as is the case with most cylindrical one-piece designs); 2) in some instances, the prismatic effect, if achieved, may not be modifiable without replacing the implant; 3) in the case of systems where the device (or part of the device) is implanted in the capsular bag, fibrosis of the capsular bag over the implant may prevent its easy replacement or rotation should the need arise for adjustment in response to a change in the PRL; 4) the size of the implant is increased such that a larger incision in the eye is required to site it (this is associated with longer wound-healing time and increased astigmatism that may adversely affect the quality of vision). In addition the high dioptric power of the lenses employed requires careful consideration of the lens surfaces so as to optimise visual potential and avoid poor performance of the implant.

Consequently there exists the need for an intraocular lens system that reliably focuses an image on the PRL, whilst also being flexible enough to allow for changes in the location of the patient's PRL without the need for further surgery.

SUMMARY OF INVENTION

According to a first aspect of the present invention there is provided an intraocular lens system comprising at least one intraocular lens having an anterior surface and a posterior surface, wherein at least one surface of the lens (and preferably both surfaces) is configured to include asphericity to provide for a continuum of retinal images to be focused at the retina in an area between two retinal eccentricities.

Some embodiments of the invention include two (or more) lenses, for example an anterior light-converging intraocular lens for positioning within the eye, the anterior lens having an anterior surface and a posterior surface; and a posterior light-diverging intraocular lens for positioning within the eye posterior to the anterior lens, the posterior lens having an anterior surface and a posterior surface; wherein at least one of the surfaces of the anterior lens and surfaces of the posterior lens are modified surfaces which include asphericity to provide for a continuum of retinal images to be presented at the retina in an area between two retinal eccentricities.

To achieve this, an optimization process is used to determine the precise values of the radius and asphericity unique to each lens surface (given for instance as the conic value of each surface). There are multiple combinations of these values (radii and conic values) that may be employed to produce a similar optical performance for different angles of retinal eccentricity. By using multiple lenses, it is possible to magnify the images presented on the retina as well as to provide the desired continuum of images in an area between two retinal eccentricities.

The area between two retinal eccentricities may be an area that extends at least 2 degrees, preferably at least 3 degrees and more preferably at least 4 degrees from the visual axis. In some embodiments the area on which retinal images are focussed extends at least 5 degrees from the visual axis. The area may extend to whole fovea.

To provide the desired image characteristics, it will normally be preferred that at least two of the surfaces include asphericity. In some embodiments, at least three of the lens surfaces include asphericity. In other embodiments all lens surfaces (i.e. all four surfaces where there are two lenses) include asphericity.

Where two lenses are used, the anterior and posterior lenses may be separate from one another. Alternatively, they may be connected to one another by a physical structure, for example to hold them at a set distance apart. In some embodiments, the two lenses can have an optical transmission element between them, which may serve to connect them.

In some embodiments, the system comprises at least two intraocular lenses (IOLs) arranged in the manner of a Galilean telescope to provide magnified images. Both lenses are centred on the visual axis. The use of asphericity provides for magnified images to be presented to the retina in an area extending 5 degrees or more from fixation. This dispenses with the need to induce a prismatic effect to target specific retinal loci, so there is no need to offset one lens in relation to the other in a direction perpendicular to the visual axis. In this way images may be focused in a continuum across the fovea (but not necessarily limited to the fovea) in individuals with poor central vision.

Optionally, a higher degree of asphericity may be conferred on any of the modified surfaces or a combination of surfaces. The tolerance of the system is advantageously increased as a result of further increasing asphericity in one of the modified surfaces. This means that the relative positioning of the two lenses is less critical and the system therefore less sensitive to variations in the separation between the two lenses that may arise, for example, due to the anatomy of the eye of the patient or differences in surgical technique. For example, the asphericity in said one of the modified surfaces may be between 2 and 4 times as great as the asphericity in one or more of the other surfaces including asphericity. Preferably, the posterior surface of the posterior lens has a higher amount of asphericity than the remaining surfaces in the system. The aberration may be any high order aberration (particularly 4th to 6th order); a spherical aberration or otherwise such that the tolerance of the IOL system is improved. The IOL system can therefore act to improve the patient's vision over a range of lens separation distances rather than at a specific separation distance. The IOL system avoids problems associated with other IOL systems where placement of the system in a patient's eye can actually result in a reduction in quality of the patient's vision due to optical effects associated with the relative locations of the two lenses.

The system advantageously permits relatively simple explanation of the lenses should the patient not tolerate the device or should it require replacement.

The use of two intraocular lenses (IOLs) in concert provides a way to maximize the visual potential of patients with age-related macular degeneration and other progressive and non-progressive conditions that affect the macula and central field of vision.

Optionally, the modified surfaces are rotationally symmetric polynomial conic surfaces, although other non-spherical surfaces may be used in other embodiments.

Optionally, the surface sag (z coordinate) of the modified surface is given by:

$$Z = \frac{cr^2}{1 + \sqrt{1 - (1+k)c^2 r^2}}$$

A possible, but not unique, combination of radii (r) and conic constants (k) is the following:

$r1 = 6.6 \text{ mm}; k1 = -9;$ $r2=-5.7$ mm;$k2=-0.6$;

$r3=-13.3$ mm;$k3=-100$;

$r4=4$ mm;$k4=-7$.

It should be noted that many other combinations of radii and conic constants may render similar values.

Preferably, the intraocular lens system comprises modification of all four lens surfaces.

Preferably, all four surfaces in the intraocular lens system are rendered aspherical.

Preferably, the intraocular lens system further includes: an anterior lens positioning means; and a posterior lens positioning means; wherein the anterior positioning means is configured such that when the anterior lens is positioned within the eye, the anterior positioning means locates the anterior lens so that it is aligned with the optical axis of the eye; and wherein the posterior lens positioning means is configured such that when the posterior lens is positioned within the eye, the posterior positioning means locates the posterior lens in so that it is aligned with the optical axis of the eye. In this way, the haptics configured in a symmetrical haptic design when in use such that the image focused onto the retina by the IOL system is focused at the fovea in an area extending between two retinal eccentricities.

Optionally, the anterior lens and the anterior positioning means is a single-piece; and/or the posterior lens and the posterior positioning means is a single-piece. For example, each lens may be moulded to include its haptics.

Optionally, the modified surfaces include a second aberration, the second aberration being a Zernike polynomial for any one of: tilt, defocus, astigmatism, or coma. This aberration may be at least a 4th order aberration. Optionally, it may be no more than a 6th order aberration.

In this way, the IOL system is further optimised to correct for additional optical aberrations of specific patients.

Preferably, one or both of the intraocular lenses is tinted yellow and thereby configured such that the lens material absorbs light having wavelengths below 390 nm. In this way, the transverse chromatic aberration is reduced thereby optimizing the optics of the system.

Optionally, optics of the lenses are modified such that magnified images may be focused on the retina at a wide angle from the foveal centre (beyond 5 degrees from the foveal centre).

Optionally a third intraocular lens with a surface incorporating a diffractive property is locatable between the first and second lens to increase the depth of focus of the system.

Optionally a third intraocular lens with a surface incorporating asphericity is locatable between the first and second lens to increase the range of eccentricities across which an image is presented at the retina.

In some embodiments, the anterior lens is suitable to be positioned in the anterior chamber of the eye and the posterior lens is suitable to be located in the ciliary sulcus of the eye. The anterior lens may have a diameter which is no more than 5 mm. Optionally, the anterior lens may have a diameter of no less than 4 mm and no more than 5 mm. In other embodiments, one or both lenses may have a diameter of no more than 6 mm. In still further embodiments, lenses of diameters greater than 6 mm may be used.

In some embodiments, the anterior lens is suitable to be positioned in the ciliary sulcus of the eye and the posterior lens is suitable to be positioned in the capsular bag of the eye. Again, the anterior lens may have a diameter which is no more than 5 mm. Optionally, the anterior lens may have a diameter of no less than 4 mm and no more than 5 mm.

In some embodiments, both the anterior lens and the posterior lens are suitable to be positioned in the capsular bag of the eye.

In some embodiments the anterior lens is suitable for positioning in the anterior chamber of the eye and the posterior lens is suitable for positioning in the capsular bag of the eye.

In some embodiments the anterior lens and the posterior lens are both suitable-for positioning in the ciliary sulcus of the eye.

Preferably at least part of a lens is made from a biocompatible material.

Preferably both lenses are made either partially or entirely from a biocompatible material.

The biocompatible material may be silicone or an acrylic. The material may be a rigid material such as polymethylmethacrylate but may be a softer acrylic which may have hydrophobic or hydrophilic properties.

Optionally, the intraocular lens system includes haptics for the anterior lens and/or posterior lens(es) which are angled to enable said lens(es) to be tilted in a variety of directions relative to the optical axis of the eye.

Optionally, the anterior lens includes an opaque annulus. This is particularly useful where the natural pupils of the patient are large as it prevents blurring of the retinal image that may otherwise occur as a result of light which travels around the outside of the lens.

Where the anterior lens is equipped with an opaque annulus, the annulus may have an inner diameter of between 5 mm and 7 mm. The annulus may be a separate feature which is connectable to the lens.

DESCRIPTION OF FIGURES

Embodiments of the current invention will be illustrated with reference to the accompanying drawings of which.

DESCRIPTION OF EMBODIMENTS

Figure 1:
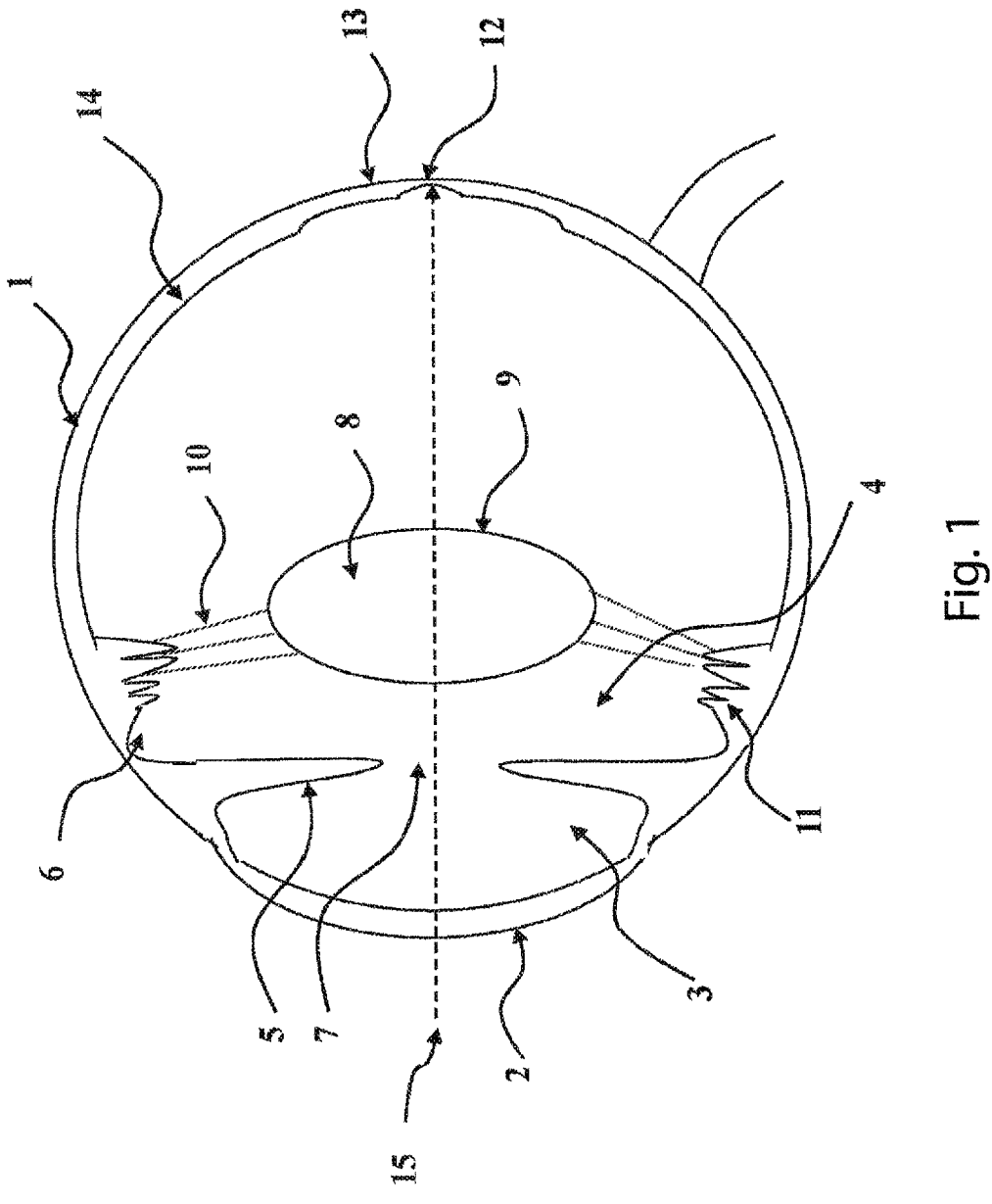
FIG. 1 is a diagrammatic cross-sectional view of an eye.

One embodiment of the present invention comprises two separate IOLs. The first is a light-converging lens shaped and sized for siting anteriorly to the second optic in the ciliary sulcus of the eye. The second is a posterior light-diverging lens shaped and sized for siting in the 'capsular bag. This embodiment is best employed with the IOLs sited in these positions but other embodiments allow for siting of the light-converging lens in the anterior chamber of the eye and the light-diverging IOL in the ciliary sulcus or both IOLs in the ciliary sulcus or both IOLs in the capsular bag. The IOLs are stabilized in their relative positions by means of haptics attached to or continuous with the optic of each lens and the configuration provides a magnified image in the manner of a Galilean telescope. However, in order to focus retinal images across a range of retinal eccentricities from the foveal centre the surfaces of the intraocular lenses are rendered aspherical. This sacrifices optimum image quality at a specific retinal locus in exchange for the ability to focus a continuum of images in an area between two retinal eccentricities-thereby dispensing with the need to induce a prismatic effect in the lens train. Furthermore, embodiments of the present invention can permit the removal of the IOLs during subsequent procedures and their replacement with IOLs based on the same design but with different dioptric powers such that more, or less, magnification of the retinal image may be provided.

An exemplary system comprises 4 rotationally symmetrical conic lens surfaces which are modified to render a continuum of images of consistent quality in an area extending up to at least 5 degrees from the foveal centre (or an area of total diameter of 10 degrees centred around the foveal centre). Preferably all 4 lens surfaces in the system are rendered aspherical with the highest amount of asphericity conferred on the posterior surface of the posterior lens. This combination optimizes the quality of the images presented to the retina of the eye across a range of retinal eccentricities and increases the tolerance of the system to errors in IOL positioning.

The flexible nature of embodiments of the present invention is made possible by optimization of the lens surfaces to correct for a range of optical aberrations. Optimisation of the IOL surfaces is required in the first instance because of the high dioptric powers of the optics, since these deviate from the thin lens paraxial formula described earlier. Each surface of the IOLs in the present invention has an aspherical surface. This affords magnified images to be presented to the fovea across a range of retinal eccentricities without the need for displacement of the two lenses relative to one another in a direction perpendicular to the visual axis. Flexibility is also afforded by the fact that there is an absence of any coupling between the two lenses of the exemplified embodiments of the present invention—thereby facilitating implantation of the IOLs without the need for a large incision in the eye that would increase astigmatism and increase recovery time. Similarly, this feature permits easier explantation of the lenses (if so desired). However, because the distance between the two lenses along the optic axis is also a critical factor in determining the quality of the retinal image, a small shift in the position of the lenses relative to one another along the optic axis results in the generation of significant refractive error and degrades the quality of the image presented to the macula. Some embodiments of the current invention overcome this problem by inducing a higher degree of asphericity in one of the four lens surfaces in the system (preferably the posterior surface of the posterior lens). This increases the depth of focus and assures both a high quality of retinal image and a significant range of positioning tolerance. Other optional modifications to either or both IOLs are included in the disclosure for the present invention; these variously include refinements to the optics, such as to reduce vignetting with larger pupils, and changes that permit a wider application of the device. It is contemplated that the kit will include a range of IOLs of varying refractive powers and surfaces to confer a range of image magnifications and use of the invention in a wide variety of patients including those with conditions other than AMD and those with high refractive errors and astigmatism.

It is a key feature of the present invention that the surfaces of each IOL optic are modelled/configured to induce spherical aberration, minimize optical aberration and increase the tolerance of IOL positioning. The surface characteristics of the intraocular lenses used in the present invention may be described using Zernike polynomials, these are a complete set of orthogonal polynomials defined on a unit circle which can be used to fit a wavefront or surface sag over a circular domain. They efficiently represent common errors such as coma and spherical aberration and are described according to the equation:

$$z(\rho,\theta) = \Sigma_{i\,...\,1}{}^{15} a_i Z_i$$

Where $\rho$ and $\theta$ represent the normalized radius and the azimuth angle respectively and $\alpha$, is the weighting coefficient for this term.

Table 1 shows the first 15 Zernike terms and the aberrations each term signifies.

TABLE 1

| i | $Z_i(\rho, \theta)$ | |
|---|---|---|
| 1 | 1 | Piston |
| 2 | $2\rho \cos \theta$ | Tilt x |
| 3 | $2\rho \sin \theta$ | Tilt y |
| 4 | $\sqrt{3}(2p^2 - 1)$ | Defocus |
| 5 | $\sqrt{6}(2p^2 \sin 2\theta)$ | Astigmatism 1st order (45°) |
| 6 | $\sqrt{6}(2p^2 \cos 2\theta)$ | Astigmatism 1st order (0°) |
| 7 | $\sqrt{8}(3p^3)$ | Coma y |
| 8 | $\sqrt{8}(3p^3 - 2p) \cos \theta$ | Coma x |
| 9 | $\sqrt{8}(\rho^3 \sin \theta)$ | Trifoil 30° |
| 10 | $\sqrt{8}(\rho^3 \cos \theta)$ | Trifoil 0° |
| 11 | $\sqrt{5}(6\rho^4 - 6\rho^2)$ | Spherical berration |
| 12 | $\sqrt{10}(4\rho^4 - 3\rho^2) \cos 2\theta$ | Astigmatism 2nd order (0°) |
| 13 | $\sqrt{10}(4\rho^4)$ | Astigmatism 2nd order (45°) |
| 14 | $\sqrt{10}(4\rho^4 \cos 4\theta)$ | Tetrafoil 0° |
| 15 | $\sqrt{10}(4\rho^4 \sin 4\theta)$ | Tetrafoil 22.5° |

For the purposes of promoting a full understanding of the principles of the present disclosure, reference will now be made to the Figures. No limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

With reference to FIG. 1, a representation of the human eye in cross-section. The eye is bounded by a tough fibrous coat, the sclera 1 which is absent anteriorly where it meets the cornea 2. The cornea 2 is a transparent structure that provides the eye with most of its focusing power and forms the anterior boundary of the anterior chamber 3. The posterior chamber 4 is separated from the anterior chamber 3 by the iris 5. At the anterior periphery of the posterior chamber lies a depression known as the ciliary sulcus 6. The iris 5 contains a round, central hole known as the pupil 7 that allows the passage of light to the natural crystalline lens 8. The natural crystalline lens 8 is contained within a thin, continuous membrane known as the capsular bag 9 and attached to the capsular bag 9 are attached numerous fine ligaments known as the zonules 10. At their peripheral extent the zonules 10 are attached to the ciliary muscle 11. Changes in the shape of the natural crystalline lens 8 are made possible by the action of the ciliary muscle 11 and forces transmitted via the zonules 10 to the capsular bag 9 (an effect known as accommodation). The natural crystalline lens 8 acts to focus light rays on the fovea 12, a highly specialised part of the macula 13 which in itself is a specialised part of the retina 14 (the light sensitive tissue at the back of the eye). The retina 14 consists of multiple layers that include a light-sensitive layer of cells known as photoreceptors. The photoreceptors that facilitate colour vision and high-resolution vision (known as cones) are most highly concentrated at the macula 13 and, most particularly, at the fovea 12—an area that is essential for reading and recognition of faces. It may be seen that damage to the fovea 12 and macula 13 may prevent light that has been focused at these sites from being detected with a consequent failure of any image being processed in the brain. Finally, the optical axis 15 is an imaginary line that defines the path along which light propagates through an optical system. For a system such as the eye the optical axis 15 passes through the centre of curvature of the cornea 2 and natural crystalline lens 8 and coincides with the axis of rotational symmetry.

Figure 2:
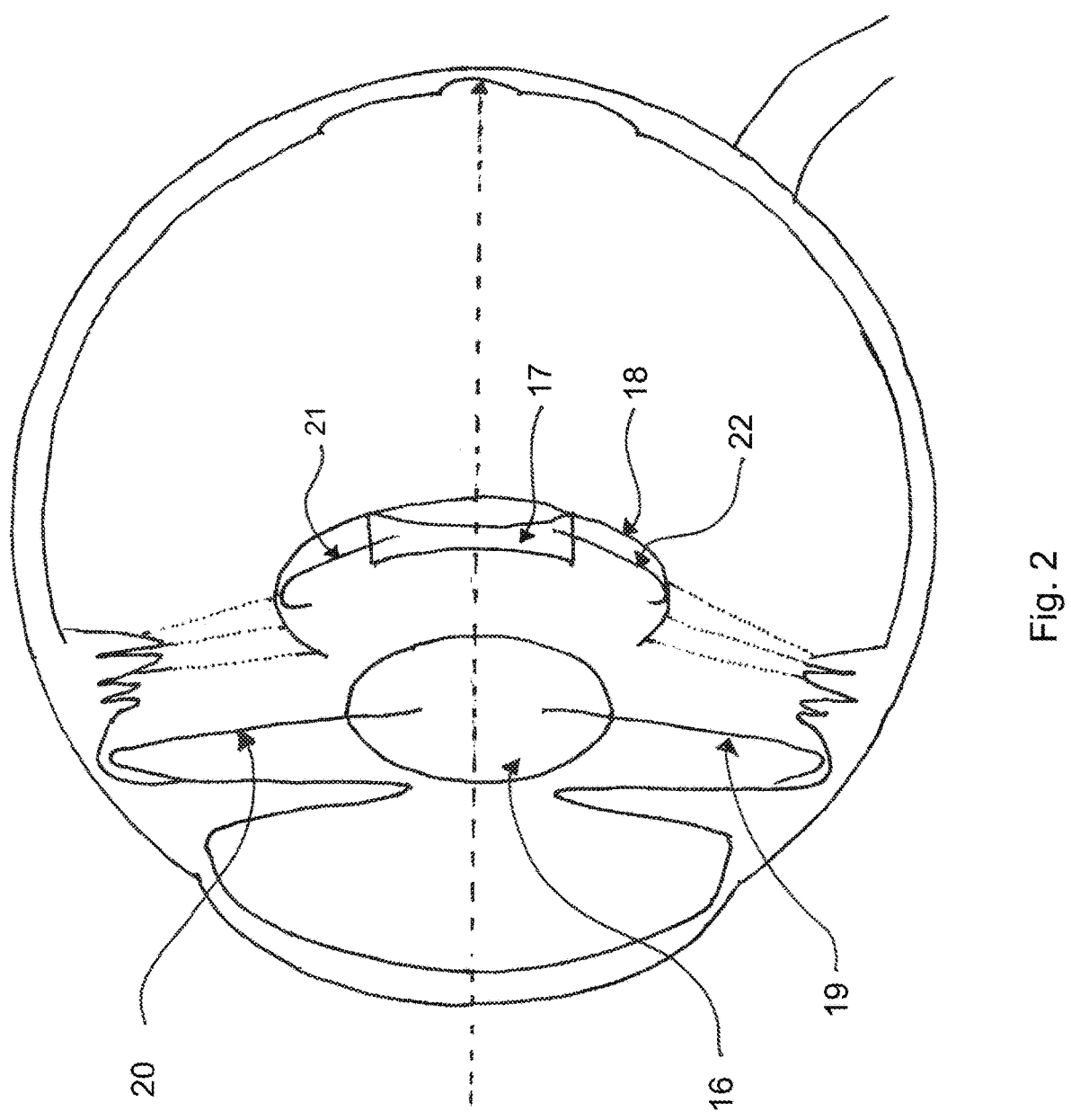
FIG. 2 is a top view and side view of the anterior IOL featured as part of the systems illustrated in FIGS. 2 and 6.

Referring now to both FIGS. 1 and 2. One embodiment of the present invention comprises an anterior light-converging IOL 16 located in the ciliary sulcus 6 and a posterior light-diverging IOL 17 located in the capsular bag 18. It should be noted that in this embodiment the capsular bag 18 contains a circular defect anteriorly to facilitate removal of the natural crystalline lens or cataract in a manner consistent with current micro-incisional techniques employed during cataract surgery. The optical component of the anterior IOL 16 is maintained in position by haptics in a symmetrical configuration such that the first haptic 19 is the same length as the second haptic 20—the optical axis of the anterior lens therefore runs in line with, that of the eye. The optic of the posterior IOL is maintained in position in the capsular bag by means of haptics attached such that the first haptic 21 is the same length as the second 22—the optical axis of the posterior lens therefore runs in line with that of the eye and that of the anterior lens. In this embodiment both optics 16, 17 are made of a hydrophobic material, such as soft acrylic polymer (refractive index 1.54; Abbe number 40; visible range transmission>92%; ultraviolet light transmission<0.5%), but generally the optics may be made from any transparent, biocompatible material used in intraocular lens construction, with calculations for optimisation of the optic surfaces (as set out below) revised accordingly. Similarly the haptics 19, 20, 21, 22 may be may be formed of any suitable polymeric material including polymethymethacrylate and/or polypropylene. The IOLs are designed to be foldable to facilitate implantation via a wound in the eye less than 5 mm in length.

Referring to FIGS. 1,2, 3, 4, 5, 6 and 7, aspects of the IOLs and their arrangement are discussed in more detail.

Figure 3:
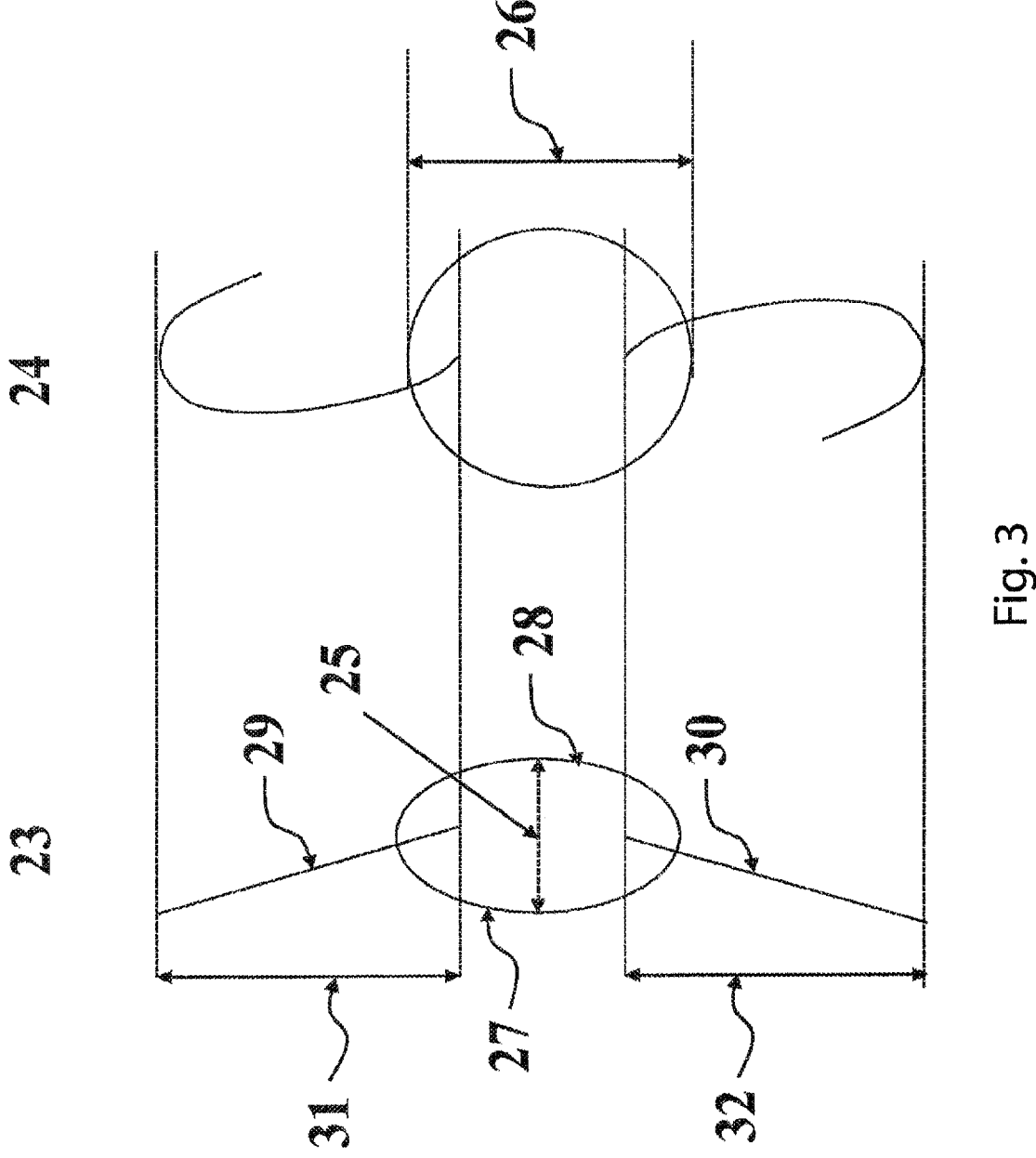
FIG. 3 a top view and side view of the posterior IOL featured as part of the systems illustrated in FIGS. 2 and 6.

FIG. 3 shows the anterior light-converging IOL in cross-section 23 and from the top 24. The anterior converging IOL consists of a light converging optic of a thickness 25, a diameter 26 and a dioptric power such that in conjunction with the posterior IOL, light may be focused to provide a retinal image of a specific magnification across a range of retinal eccentricities at the macula. To achieve a retinal image of sufficient quality to benefit an individual with poor central vision, the optical design of the first lens is optimized such that it consists of an aspheric anterior surface 27 and an aspheric posterior surface 28. Each surface of the first lens is a rotationally symmetric polynomial aspheric conic surface for which the surface sag (z co-ordinate) as a function of the radial coordinate r can be given by:

$$Z = \frac{cr^2}{1 + \sqrt{1 - (1+k)c^2r^2}}$$

Wherein, i) c is the inverse of the radius of curvature R: c=1/R ii) k is the conical constant (with a value ranging between −1 and 0 iii) a is an aspheric polynomial coefficient, additional to the conical constant The first lens is centred in line with the optical axis of the eye by means of two haptics that are attached to or continuous with the anterior optic such that the first haptic 29 is the same length as the second haptic 30. The optic is therefore sited equidistant 31, 32 from the point at which each haptic is designed to make contact with the eye 6. It should be noted that in this embodiment both haptics are angled anteriorly from the point at which they emerge from the optic in such a way that the optic is sited in a plane that lies posterior to that of the ciliary sulcus—in this way the anterior surface of the anterior IOL remains clear of the iris 5. However, the haptics may be designed for positioning of the optic in the anterior chamber 3, the ciliary sulcus 6 or the capsular bag 9 of the eye.

Figure 4:
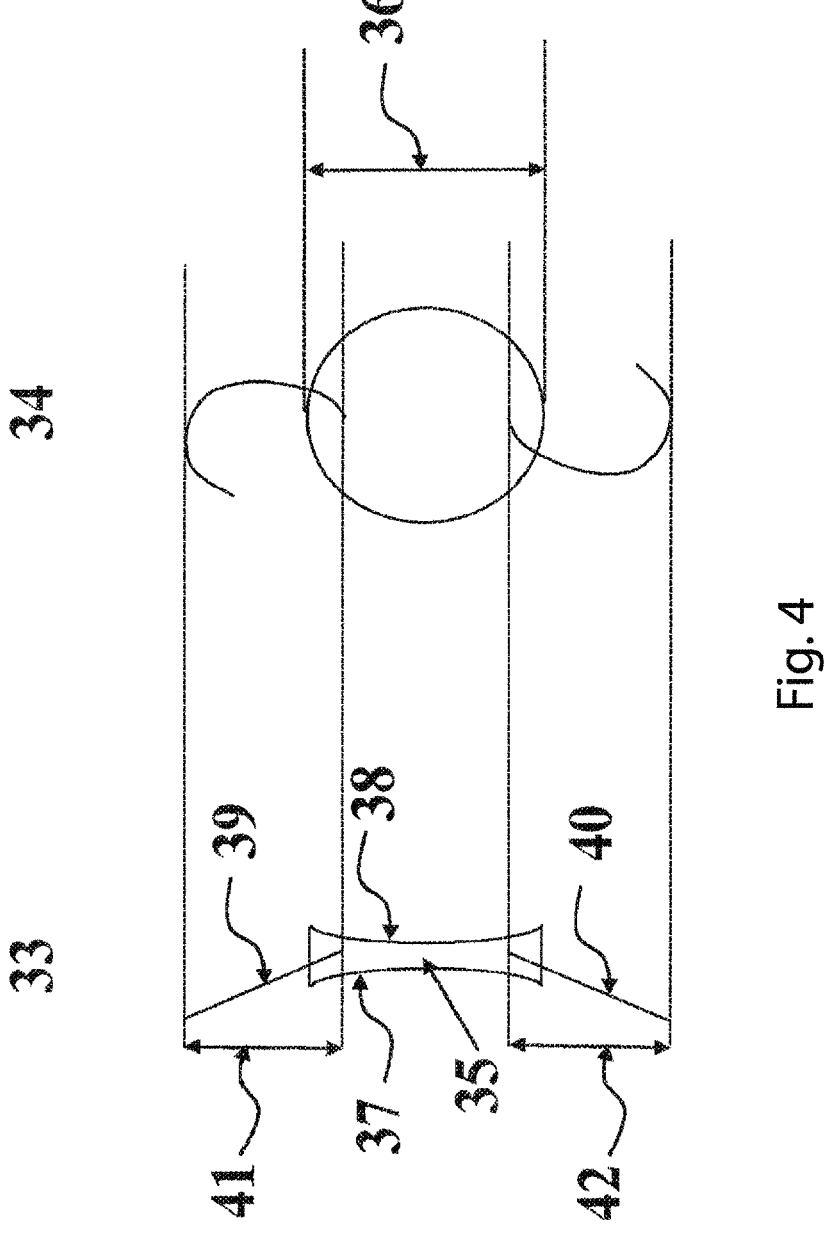
FIG. 4 is a diagrammatic cross-sectional view of an eye featuring an embodiment of the current invention as set out in the present disclosure.

With reference to FIG. 4, the posterior light-diverging IOL is shown in cross-section 33 and from the top 34. The posterior light-diverging IOL consists of a light-diverging optic of a central thickness 35, diameter 36 and dioptric power such that in conjunction with the anterior IOL, light may be focused on a region of the macula to provide retinal images of a specific magnification. Again, to achieve retinal images of sufficient quality with this configuration the optical design of the posterior optic is optimised such that it consists of a rotationally symmetric polynomial aspheric anterior surface 37 and a rotationally symmetric polynomial aspheric conic posterior surface 38. For each surface the surface sag z as a function of the radial coordinate r can be given by expression:

$$Z = \frac{cr^2}{1 + \sqrt{1 - (1+k)c^2r^2}}$$

as with the anterior optic.

By way of example only, the conical constants (k) in one embodiment of the invention may be (starting with the anterior surface of the anterior optic):

First surface: −9

Second surface: −0.6

Third surface: −110

Fourth surface: −7

Figure 5:
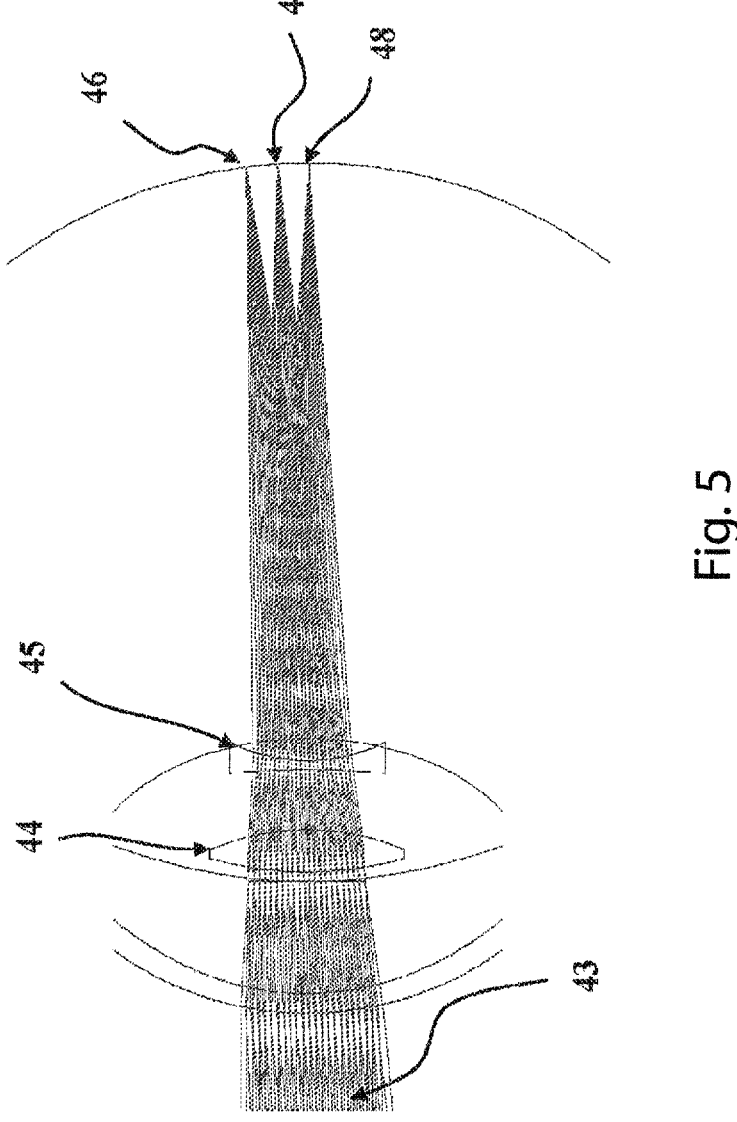
FIG. 5 is a diagrammatic cross-sectional view of an embodiment of the present invention in an eye and associated light ray traces.

Attached to or continuous with the posterior optic are two haptics 39, 40 of equal length 41, 42. The haptics may be designed for positioning of the optic in the anterior chamber 3, the posterior chamber 4 or the capsular bag 9 of the eye. It should be noted that in order to achieve a maximal distance from the anterior IOL it may be necessary to angle the haptics 39, 40 attached to the posterior IOL such that the optic lies in a plane posterior to the site where the haptics make contact with the periphery of the capsular bag 18. With reference to FIGS. 2 and 5, that show cross-sections of the arrangement of the anterior IOL in relation to the posterior IOL: The IOLs are arranged in the eye in line with the optical axis of the eye such that the anterior light-converging IOL 46 is sited at an optimal distance from the posterior light-diverging IOL 47 resulting in a magnification of the retinal image of 1.2 to 1.4.

Figure 6:
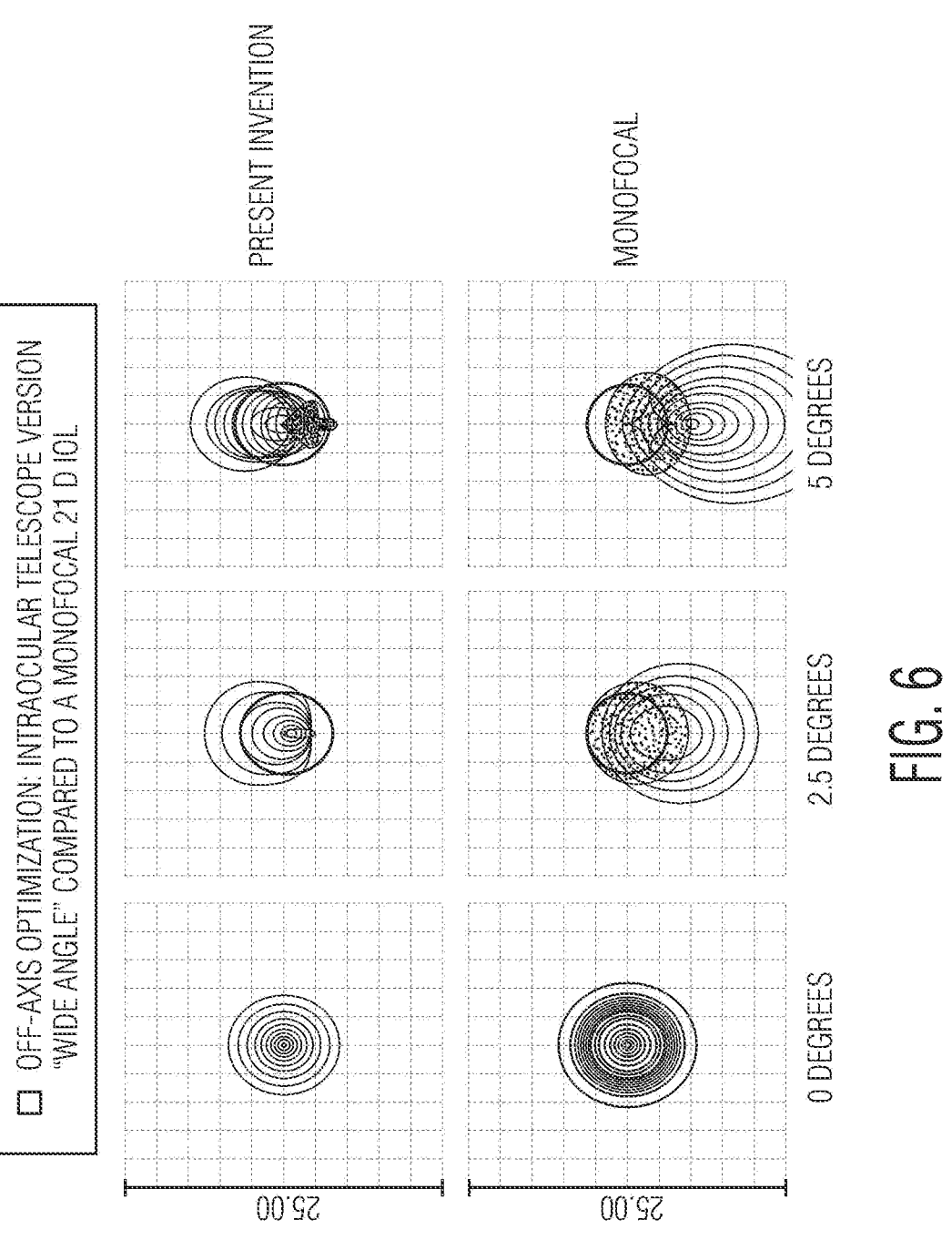
FIG. 6 shows the off-axis image quality delivered by the present invention compared with that provided by a standard monofocal optic.
Figure 7:
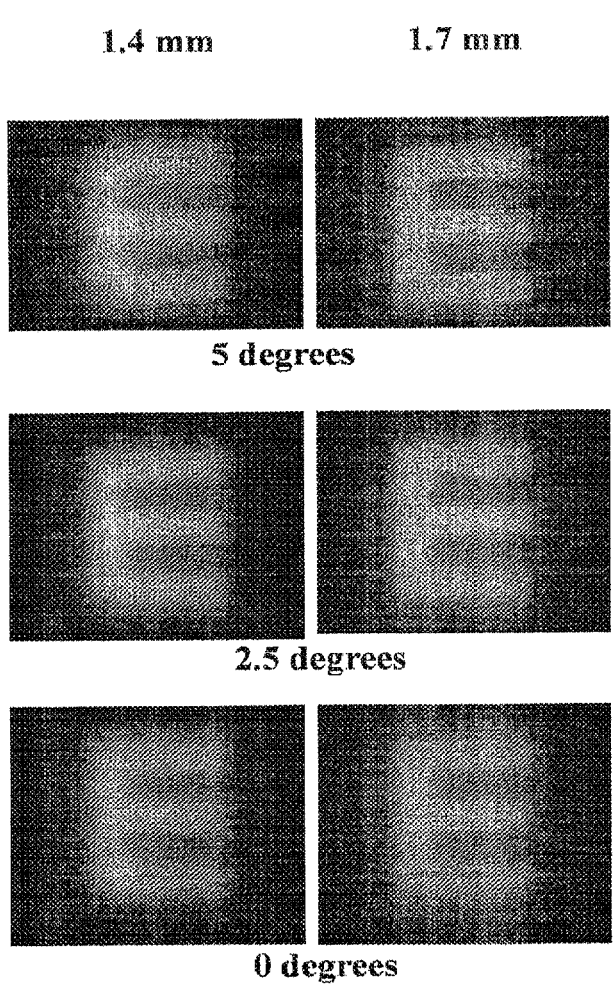
FIG. 7 demonstrates the consistent image quality provided by the present invention in the range of 0 to 5 degrees of eccentricity from fixation at the retina and with the distance between the two optics of the system varying from 1.4 mm to 1.7 mm.

With reference to FIG. 1, FIG. 5, a diagrammatic representation of the present invention in a cross-section of the eye and lines representing the path of light 43 taken in the eye on entering the cornea and passing through the optics of the present invention 44, 45 and FIG. 6. The optic of the first lens 44 is sited anteriorly to that of the optic of the second lens 45 in the manner of a Galilean telescope and both lenses are centred with their optical axes in line with that of the eye 15. The surfaces of each optic are rendered aspheric such that a magnified image is simultaneously presented across a range of eccentricities at the retina 46, 47, 48. The present invention is optimised to render an image of similar optical quality in an area 10 degrees off-axis (an area with a radius of 5 degrees from the foveal centre). FIG. 6 demonstrates the off-axis optimization of image quality achieved by the present invention at eccentricities of 0, 2.5 and 5 degrees from fixation when compared with that obtained with a standard 21 dioptre monofocal optic. The effect is such that a magnified image may be presented at a patient's preferred retinal locus without the need to target this area of the retina specifically and without requiring the patient to learn to fixate eccentrically. Furthermore, if the preferred retinal locus of the patient changes over time they may gradually learn to make use of an image presented at a different retinal eccentricity from that used initially.

Since even a small deviation from the intended axial positioning of the two implants relative to one another could produce a significant refractive error and degradation of the image presented at the retina, the current invention increases the tolerance of the system for sub-optimal implant axial positioning by rendering one of the surfaces in the system, preferentially the posterior surface of the second lens 38, more aspherical than the other optical surfaces in the system. This adds aberration and increases the depth of focus of the present invention. The precise amount of added aberration is determined to assure both a good enough quality of retinal image and a significant range of positioning tolerance. This feature of the present invention ensures that it is capable of delivering a high quality of retinal image whilst accommodating variations in the practice of individual surgeons and alterations in the anatomy of the eye during the early and late post-operative periods. The benefits of added aberration, in increasing the tolerance of IOL positioning in the present invention and the quality of the image presented at the retina across a range of eccentricities by the present invention, are both shown in FIG. 7. It may be seen that a similar image quality is delivered at angles of eccentricity ranging from 0 to 5 degrees and that the quality is maintained when the distance between the two lenses varies from 1.4 mm to 1.7 mm.

The optics of the system are further optimised to take account of transverse chromatic aberration induced by the vertical displacement of the implants relative to one another 51, this is achieved by adding a yellow tint to the implants during the manufacturing process. The addition of a yellow tint to the IOLs also confers the added benefit of macular protection from ultraviolet radiation.

With reference to Table 1, it can be seen that the surfaces of the optics of the IOLs of the present invention may be further optimised by the addition of values for Zernike polynomials, besides those for spherical aberration. The surfaces may be expressed as a linear combination of Zernike polynomials including those for tilt, defocus, astigmatism, and coma, such that optical aberrations for individual patients are minimised. Consequent remodelling of the lenses means that at least one lens design parameter is changed—this may include the anterior surface shape and central radius and the posterior surface shape and central radius—and IOLs may be selected from a kit of lenses to achieve the desired effect.

Figure 8:
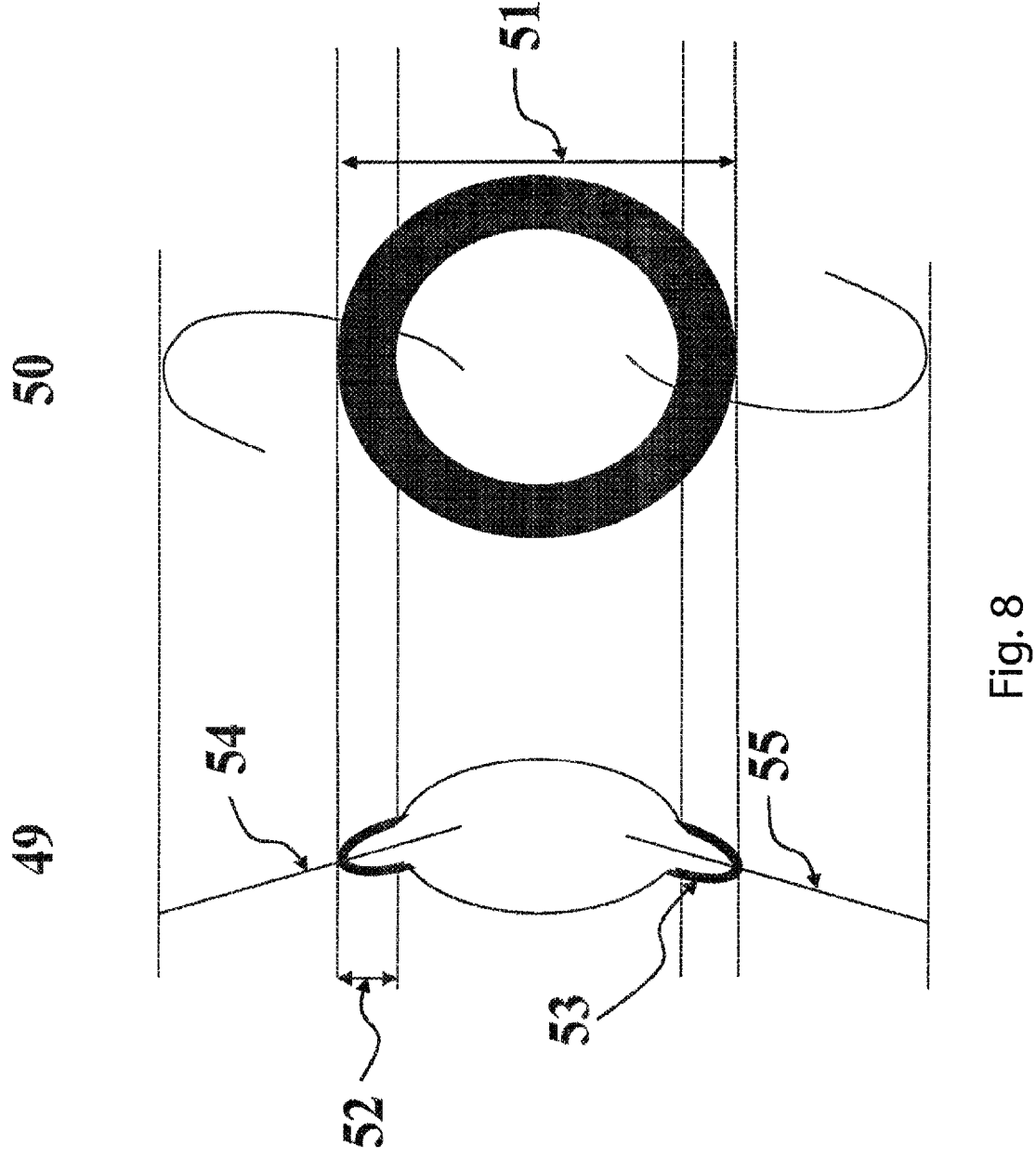
FIG. 8 is a top view and side view of an embodiment of the anterior IOL.

The materials, biomechanical properties, lengths and shapes of the haptics and the materials, surfaces, sizes and biomechanical properties of the anterior and posterior optics may be modified to achieve the desired retinal image (the haptics may form part of a single piece anterior or posterior IOL for example and may be permit siting of either lens or both lenses in the anterior chamber 3, posterior chamber 4 or capsular bag of the eye 9). It is further contemplated that a range of anterior and corresponding posterior implants, consisting of a range of dioptric powers, optical surfaces, optic tints and haptic configurations may be included in the kit to facilitate targeting of the PRL in individual patients with a wide range of refractive errors (this includes toric optics to correct for high astigmatism). Referring now to FIG. 8 which shows a version of the anterior light-converging IOL in cross-section 49 and from the top 50. It is contemplated that with the current invention there is risk of visually significant vignetting occurring with larger pupil sizes, particularly where levels of vertical decentration between the anterior and posterior IOLs are high. A version of the anterior light-converging IOL designed to prevent such vignetting is shown 49, 50. The diameter of the optic is increased in this embodiment 51 with an added rim 52 rendered opaque by the application of a biocompatible and stable opaque paint to its surface 53.

Figure 9:
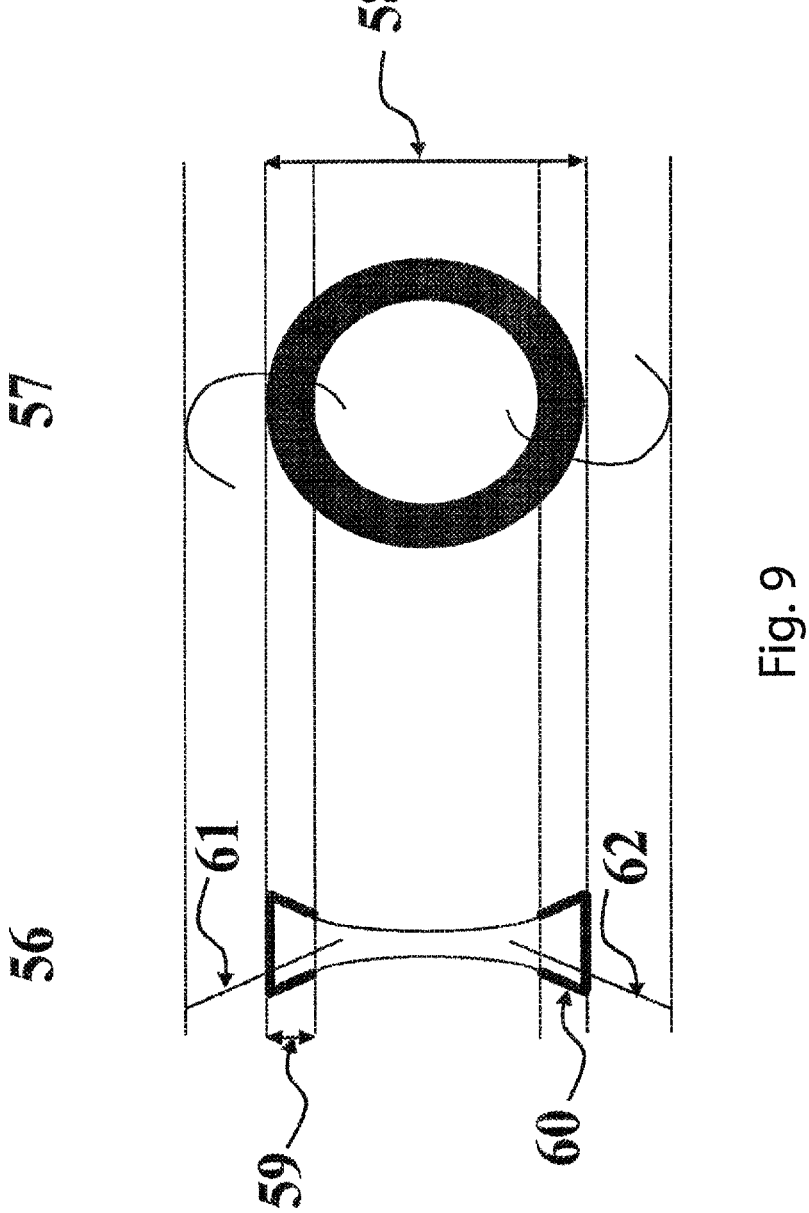
FIG. 9 is a top view and side view of an embodiment of the posterior IOL.

Alternatively an opaque, rim may be located on the surface of the optic, for example bonded to the optic as originally conceived to create the same effect. The rim is of sufficient width to prevent vignetting with larger pupils. The refractive part of the optic remains unaffected and the haptics 54, 55, which are of equal lengths, insert into the optic as previously described. With reference to FIG. 9, which shows a version of the posterior light-diverging IOL in cross-section 56 and from the top 57; the same, or a similar, effect may be achieved by increasing the diameter of the posterior optic 58 to include a rim 59 that may be opaque and bonded to the optic or, as shown in the illustration, rendered opaque by means of a biocompatible and stable opaque paint applied to its surface 60 (the configuration of the haptics remaining unchanged 61, 62).

In a further embodiment (not shown) the opaque rim may be located within part of the optic body.

Although the invention is described in the preferred embodiments illustrated in the Figures attached, no restriction is intended by this. The design and configuration of the optical surfaces, including application of a tint to refine optical properties, are considered integral to the present invention and may be applied in a variety of circumstances. For example it is contemplated that an arrangement of the IOLs may include positioning of the anterior light-converging IOL in the anterior chamber 3 and the posterior light-diverging IOL in the posterior chamber 4 or both IOLs in the posterior chamber or both IOLs in the capsular bag 9 with revision of the optical surfaces, IOL dioptric powers and haptic designs accordingly.

Further embodiments (not shown) include the application of diffractive surfaces to one optic or both optics to permit a range of focal points in the eye (and consequently uncorrected distance and near vision); and targeting of the PRL—or the introduction of a third optic with one of the aforementioned characteristics, to either the anterior chamber, the posterior chamber or the capsular bag.

Again, whilst reference to use of the present invention in subjects with AMD is made, no restriction in terms of its use is intended. It is contemplated that the present invention will be used in a wide variety of clinical scenarios to achieve targeting of areas of the macula eccentric to fixation and with a range of magnification and refractive capabilities. The present invention is designed for insertion into the eye via a small (5 mm) incision with or without use of a cartridge injector, an approach consistent with its use in the context of surgical techniques employed during natural crystalline lens or cataract extraction. As such it is expected that the present invention may be used in combination with natural crystalline lens extraction or at the time of cataract surgery or, if necessary, subsequent to cataract surgery/lens extraction (with its application-together with any necessary modifications to the optic surfaces, haptic design, optic materials and optic dioptric power-in addition to or instead of pre-existing implants in the eye).

In keeping with this approach, a range of monofocal IOLs may be provided that is designed for use in cases where the present invention is not indicated at initial surgery, but where the natural crystalline lens is removed and the patient wishes to retain the potential to use the present invention at a later date. Under these circumstances, the optics of the monofocal IOL implanted at the first operation will be optimised for use in conjunction with the present invention should this be required in the event that the patient develops a macular disease.

A wide range of modification and substitution is contemplated with regards to the present disclosure, and the illustrations provided are not intended to restrict the design of the present invention or limit the applications of its use. Furthermore it is intended that a variety of permutations of the present invention may be created by incorporating the various properties as laid out in the Claims attached.

The invention claimed is:

1. A lens comprising:
an anterior surface comprising a rotationally symmetrical polynomial conic surface;
a posterior surface comprising a rotationally symmetrical polynomial conic surface; and
a plurality of haptics having a symmetrical design and comprising ciliary-sulcus-engaging surfaces configured to position the lens within a ciliary sulcus of an eye and align the lens with an optical axis of the eye;
wherein at least one of the anterior surface and the posterior surface are aspherical surfaces configured to induce spherical aberration while minimizing optical aberration and thereby provide for a continuum of retinal images to be simultaneously focused at an area of a retina of the eye across a range retinal eccentricities.

2. The lens of claim 1, wherein the anterior surface and the posterior surface are configured to converge light onto a posterior light-diverging intraocular lens of the intraocular lens system.

3. The lens of claim 2, wherein one or both of the lens and the posterior light-diverging intraocular lens are configured to generate a magnified image that is focused on the retina at a wide angle of more than 5 degrees from the foveal center.

4. The lens of claim 2, wherein one or more of the lens and the posterior light-diverging intraocular lens comprise a biocompatible material.

5. The lens of claim 4, wherein the biocompatible material comprises silicone or polymethylmethacrylate.

6. The lens of claim 1, wherein a first aspherical surface of the aspherical surfaces has a higher degree of asphericity, as compared to a second aspherical surface of the aspherical surfaces, so as to increase the depth of focus.

7. The lens of claim 1, wherein at least one aspherical surface of the aspherical surfaces has a surface sag (z coordinate) given by:

$$Z = \frac{cr^2}{1 + \sqrt{1 - (1 + k)c^2 r^2}}$$

wherein:
r is a radial coordinate,
k is a conical constant, and
c is an inverse of a radius of curvature.

8. The lens of claim 1, wherein at least one aspherical surface of the aspherical surfaces comprises a surface having an aberration, the aberration comprising a Zernike polynomial for any one of: tilt, defocus, astigmatism, or coma.

9. The lens of claim 1, wherein the lens and the plurality of haptics are formed of a single piece of soft acrylic polymer.

10. The lens of claim 1, wherein the lens comprises a biocompatible material.

11. The lens of claim 10, wherein the biocompatible material comprises silicone or polymethylmethacrylate.

12. The lens of claim 1, wherein the lens is tinted yellow.

13. The lens of claim 1 further comprising an opaque rim.

14. A lens comprising:
an anterior surface comprising a rotationally symmetrical polynomial conic surface;
a posterior surface comprising a rotationally symmetrical polynomial conic surface; and
a plurality of haptics having a symmetrical design and comprising ciliary-sulcus-engaging surfaces configured to position the lens within a ciliary sulcus of an eye and align the lens with an optical axis of the eye;
wherein at least one of the anterior surface and the posterior surface are aspherical surfaces configured to induce spherical aberration while minimizing optical aberration and thereby provide for a continuum of retinal images to be focused at an area of a retina of the eye between two retinal eccentricities, and
the anterior surface and the posterior surface are configured to converge light onto a posterior light-diverging intraocular lens of an intraocular lens system, wherein the posterior light-diverging intraocular lens comprises:
a second anterior surface;
a second posterior surface; and
a plurality of posterior haptics having a symmetrical design and comprising capsular-bag- engaging surfaces configured to position the posterior light-diverging intraocular lens in a capsular bag of the eye and align the posterior light-diverging intraocular lens with the optical axis of the eye.

* * * * *